United States Patent
He et al.

(10) Patent No.: US 6,688,551 B1
(45) Date of Patent: Feb. 10, 2004

(54) METHODS AND APPARATUS FOR TOILET PAPER ROLL HOLDER VAPOR DISPENSER

(75) Inventors: Mengtao Pete He, Scottsdale, AZ (US); Carl Triplett, Scottsdale, AZ (US); Paul Pappalardo, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/295,134

(22) Filed: Nov. 15, 2002

(51) Int. Cl.$^7$ ............................................... B65H 75/18
(52) U.S. Cl. ..................... 242/599; 242/905; 239/52; 428/905
(58) Field of Search .................. 242/596.4, 596.5, 242/596.7, 905, 598, 598.2, 598.3, 598.4, 599.1; 428/905; 239/44, 52

(56) References Cited

U.S. PATENT DOCUMENTS

| | | | |
|---|---|---|---|
| 649,062 A | * 5/1900 | Levett | 242/599.1 |
| 1,552,082 A | * 9/1925 | Riley | 239/52 |
| 1,644,503 A | 10/1927 | Aumack | |
| 1,794,016 A | 2/1931 | Henry | |
| 2,293,785 A | 8/1942 | Wintz | |
| 2,546,820 A | 3/1951 | Grant | |
| 2,639,939 A | 5/1953 | Matchett | |
| 2,728,604 A | 12/1955 | Garfeld | |
| 2,746,798 A | 5/1956 | Wardell, Jr. | |
| 2,753,209 A | 7/1956 | Klasky | |
| 2,806,738 A | * 9/1957 | Tsakalas | 239/52 |
| 2,946,511 A | 7/1960 | Bartus | |
| 3,002,704 A | 10/1961 | Grossfield | |
| 3,017,117 A | 1/1962 | Klingler | |
| 3,329,367 A | 7/1967 | Paradiso | |
| 3,565,339 A | 2/1971 | Curran | |
| 3,601,328 A | 8/1971 | McClung | |
| 3,771,883 A | * 11/1973 | Terepin | 242/905 |
| 3,830,198 A | 8/1974 | Boone | |
| 3,837,574 A | 9/1974 | Curran | |
| 3,848,822 A | 11/1974 | Boone | |
| 4,110,261 A | * 8/1978 | Newland | 428/905 |
| 4,124,259 A | 11/1978 | Harris | |
| 4,191,342 A | 3/1980 | Reinhold | |
| 4,286,754 A | * 9/1981 | Jones | 239/44 |
| 4,314,678 A | 2/1982 | Upchurch | |
| 4,565,336 A | 1/1986 | Hefty et al. | |
| 4,759,510 A | 7/1988 | Singer | |
| 4,901,889 A | 2/1990 | Mitchell | |
| 4,925,102 A | 5/1990 | Jones et al. | |
| 5,071,704 A | * 12/1991 | Fischel-Ghodsian | 428/905 |
| 5,165,620 A | 11/1992 | Kampiziones | |
| 5,170,938 A | 12/1992 | Dewing | |
| 5,381,984 A | 1/1995 | Hindsgual | |
| 5,494,218 A | 2/1996 | Armand | |
| 5,598,987 A | 2/1997 | Wachowicz | |
| 5,624,025 A | 4/1997 | Hixon | |
| 5,727,751 A | 3/1998 | Liu | |
| 5,758,843 A | 6/1998 | Ongaro | |
| 5,873,529 A | 2/1999 | Johnson | |
| 6,000,658 A | 12/1999 | McCall, Jr. | |
| 6,367,734 B1 | 4/2002 | Cartwright | |
| 6,378,800 B1 | 4/2002 | Apichom | |
| 6,425,530 B1 | 7/2002 | Coakley | |
| 6,572,051 B1 | * 6/2003 | Stude | 242/598.2 |
| 6,575,383 B2 | * 6/2003 | Dobler et al. | 239/52 |

OTHER PUBLICATIONS

US 4,497,456, 2/1985, Crapser (withdrawn)

* cited by examiner

*Primary Examiner*—William A. Rivera
(74) *Attorney, Agent, or Firm*—Snell & Wilmer LLP

(57) ABSTRACT

The present invention provides a toilet paper roll holder vapor-dispensing device configured with an internal material delivery system and high intensity volatizable material. A toilet paper roll holder vapor-dispensing device is configured to increase dispensation of a fragrance when toilet paper is taken off the toilet paper roll through a number of configurations such as using high intensity fragrance (e.g., scented oil). The toilet paper roll holder is configured to be substantially stationary when toilet paper is removed from a roll of toilet paper supported by the holder.

30 Claims, 5 Drawing Sheets

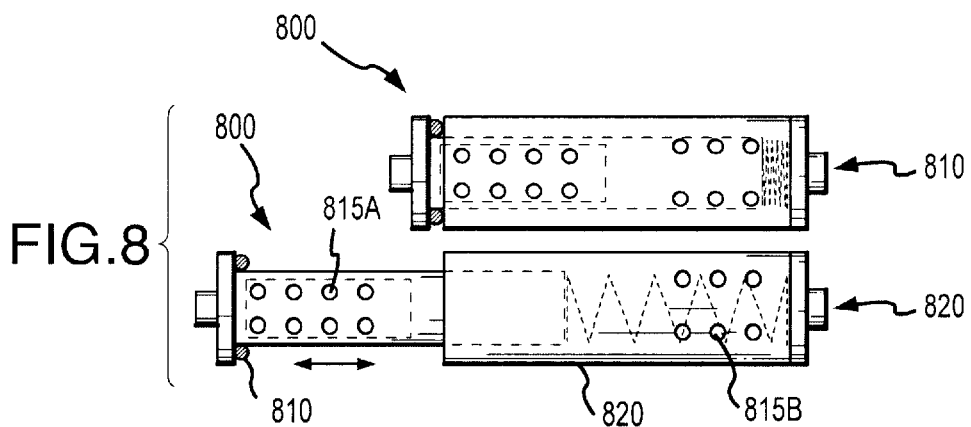
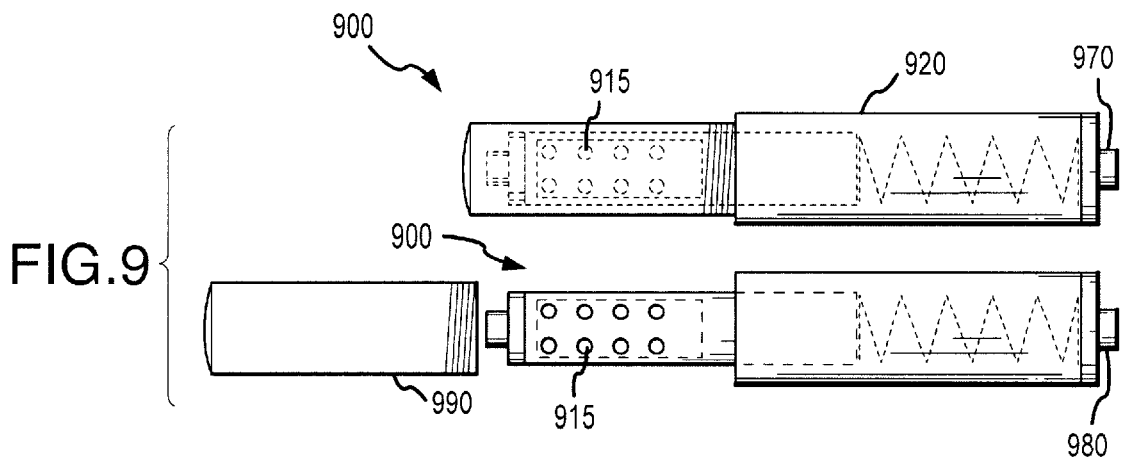
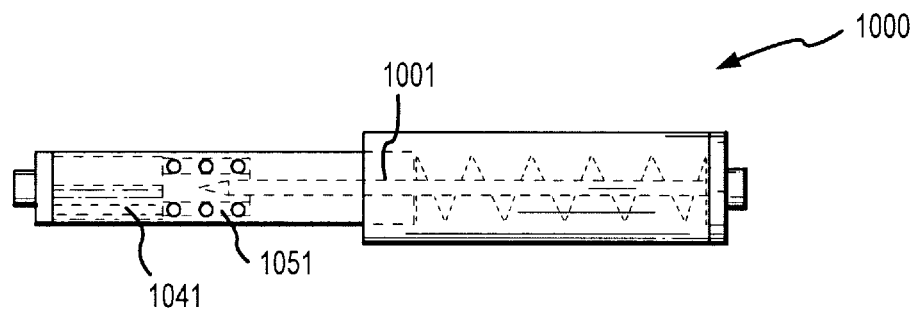
FIG.10

METHODS AND APPARATUS FOR TOILET PAPER ROLL HOLDER VAPOR DISPENSER

FIELD OF INVENTION

The present invention generally relates to vapor-dispensing devices and, more particularly, to a toilet paper roll holder vapor-dispensing device.

BACKGROUND OF THE INVENTION

Toilet paper roll holders that emit fragrance are desirable. However, there exists a need for an apparatus for dispensing fragrance that can provide, during dispensing of toilet paper, an increased rate of fragrance delivery while remaining concealed in the embodiment of a toilet paper holder. In the past, these results have been difficult to obtain given the size constraints associated with a typical toilet paper roll.

A typical toilet paper roll has a one and one-half to two inch interior diameter, and toilet paper roll holders generally have a smaller outer diameter than the smallest interior diameter of standard toilet paper rolls. Furthermore, toilet paper roll holders are generally five to seven inches in length. The available space may be further reduced because toilet paper roll holders generally are configured to be compressible for installation, creating unusable space. In addition, an internal spring(s) often occupies more of the little remaining interior space. Thus, the space available within a toilet paper roll holder for use as an air freshening apparatus is very limited.

In light of these tight space constraints, it is not surprising that some air freshening devices associated with toilet paper roll holders, are configured with all, or a portion, of the air freshening device placed external to the toilet paper roll holder. For example, U.S. Pat. No. 5,381,984 (external fan), U.S. Pat. No. 2,746,798 (external pump spray), and U.S. Pat. No. 5,170,938 (decorative end cap for the toilet paper roll) disclose devices where the air freshening material and/or the air freshening delivery mechanism exists external of the toilet paper roll holder. A less noticeable and more aesthetically pleasing fragrance emitting device is desirable.

Nonetheless, some fragrance emitting toilet paper roll holder devices have entirely enclosed the air freshening device within the toilet paper roll holder with varying degrees of success. For example, various toilet paper roll holder air fresheners have placed solid materials in the holder to emit fragrance. These devices utilize materials such as pellets, tablets, or a solid mass. However, often the fragrance emitting substance used has a relatively low rate of delivery of fragrance. Furthermore, again due to the limited size of the toilet paper roll holder, the amount of material is restricted. Thus, the strength of the fragrance emissions in these devices is typically limited and unsatisfactory. In addition, these devices do not generate an increased output of fragrance when toilet paper is removed from the roll. Also, it is not visually obvious when the fragrance is gone from pellets, tablets or solid masses.

In an effort to achieve a suitable level of fragrance delivery and an increased fragrance delivery during toilet paper removal from the roll, some toilet paper roll holders have been designed to roll. For instance, U.S. Pat. No. 4,497,456 ("the '456 patent"), states that "free rolling of the paper roll holder can increase the outflow of air-treating vapors from air-treating materials contained within the holder, particularly if the contained materials are free to tumble within the holder upon rolling." The '456 patent teaches that the rolling action of the holder and the tumbling action of the vaporizable air treating pellets are the mechanisms needed to enhance vaporization, and moreover to enhance vaporization when such air treating vapors are needed.

These rolling toilet paper roll holder design efforts are a product of the incorrect assumption that non-rolling toilet paper roll holders cannot dispense high intensity fragrance, and cannot increase the rate of dispensing when toilet paper is being removed from the roll. The '456 patent states explicitly, in its criticism of U.S. Pat. No. 2,753,209 ("the '209 patent"), that the '209 patent's toilet paper roll holder "does not very well dispense increased amounts of air-treating vapors when such are needed" and that "[t]he rate of vapor dispensing from such devices is substantially constant even while paper is being pulled from rolls mounted on such devices, an action that often occurs when undesirable odors are present." Such rolling toilet paper roll holder devices are typically complex, have a higher chance of failure, and are expensive. For example, this complexity is due to design elements that are included to make the holder roll with the toilet paper roll. These design elements include stress relaxation springs, low friction contact with the support brackets holding the toilet paper roll holder, and friction creating devices such as bumps and the like.

The '456 patent teaches that to achieve an increase in intensity of fragrance at the time of usage of the toilet paper, the holder must be free rolling and preferably exhibit tumbling of the vaporizable materials. Thus, the '456 patent identifies plastic beads or other materials that can tumble freely within the holder upon rotation thereof. Thus, the teachings associated with rotating toilet paper roll holders expressly limit the choices of substances and mechanisms for delivery of fragrance materials.

In general, prior art toilet paper roll holders that can freely rotate are complicated, more likely to malfunction or break, and more costly to manufacture than standard toilet paper roll holders. A simpler device for achieving high fragrance output and an increased fragrance output upon use of the toilet paper is desirable. Thus, there is a need for a vapor-dispensing device that overcomes these and other limitations of the prior art.

SUMMARY OF THE INVENTION

While the way that the present invention addresses the disadvantages of the prior art is discussed in greater detail below, in general, the present invention provides a toilet paper roll holder vapor-dispensing device configured with an internal material delivery system and high intensity volatizable material. In accordance with one aspect of the present invention, a toilet paper roll holder vapor-dispensing device is configured to increase dispensation of a fragrance when toilet paper is taken off the toilet paper roll through a number of configurations such as using high intensity fragrance (e.g., scented oil). In accordance with another aspect of the present invention, the toilet paper roll holder is configured to be substantially stationary when toilet paper is removed from a roll of toilet paper supported by the holder.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

FIGS. 8–10 are exemplary activation mechanisms in accordance with various exemplary embodiments of the present invention.

DETAILED DESCRIPTION

Figure 1:
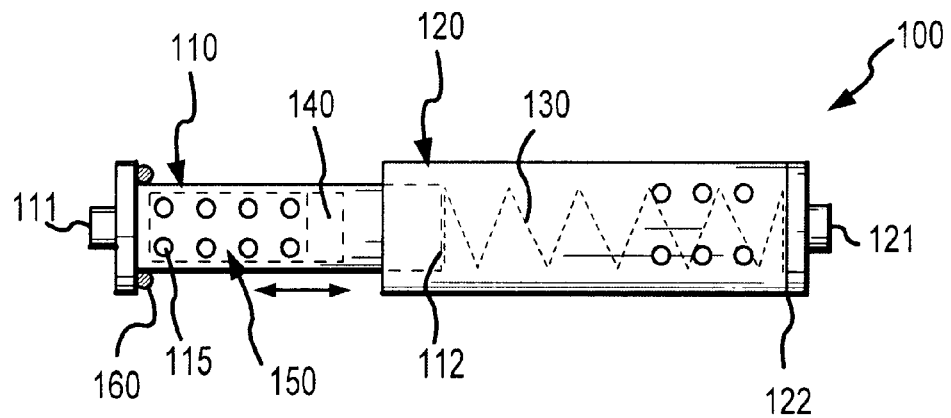
FIG. 1 is a cross-sectional view of an exemplary toilet paper roll holder vapor-dispensing device in accordance with an exemplary embodiment of the present invention.

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth in the appended claims. For example, in the context of the present invention, the method and apparatus hereof find particular use in connection with air freshening vaporizer systems. However, generally speaking, various volatizable materials such as deodorizers, sanitizers, and/or the like are suitable for use in accordance with the present invention. Likewise, though various portions of the specification refer to high intensity scented oils as the volatizable material used herein, various other materials now known or as yet unknown, having similar properties should be considered within the scope of the present invention.

In general, in various embodiments, the present invention provides a toilet paper roll holder vapor-dispensing device ("holder") configured to deliver a high intensity fragrance output without rolling of the holder or tumbling of the fragrance material Also; the holder may be configured to increase dispensation of fragrance when the toilet paper roll moves. For example, in one embodiment of the present invention, the holder is configured to deliver a fragrance at an increased rate when toilet paper is removed from a toilet paper roll on the holder. In addition, the toilet paper roll holder vapor-dispensing device is configured to discretely enclose the fragrance delivery system within the toilet paper roll holder.

Thus, in contrast to generally complex devices that attempt to use rolling of the holder itself and tumbling of the fragrance material to achieve an increased fragrance level and rate, a simple non-rolling toilet paper roll holder is configured with high intensity fragrance emitting materials. Therefore, in various embodiments, a small amount of volatizable material delivers fragrance at a relatively high rate such that a fragrance delivery device can be located within the small confines of typical toilet paper roll holders. For example, the use of very strong fragrance permits the use of a simple toilet paper roll holder that does not require rolling to deliver sufficient fragrance.

Briefly, the term "high intensity" may be characterized in various different ways including human perception, rates of dispensation, and/or the like. For example, high intensity may be defined through testing of fragrance perception in a group of people. The intensity may include such factors as the ability to overcome certain odors. Other systems for characterizing high intensity fragrance may include the amount of fragrance material dispersed over a period of time. For example, a high intensity fragrance material might comprise one or more of various scented oils. Various rates of dispensation of fragrance material may also characterize high intensity fragrance. Such rates may depend on the type of fragrance, pungency of the fragrance, the material delivery system performance, and/or other factors. Various high intensity fragrance emitting substances may also be used in the present invention.

Furthermore, normal removal of toilet paper from the non-rolling toilet paper roll holder is sufficient to increase the rate of delivery of fragrance. This increase may similarly be characterized by human perception tests, quantification techniques, and/or the like. In addition, the use of a non-tumbling delivery mechanism expands the possible fragrance substances that may be used.

In this context, FIG. 1 illustrates a cross-sectional view of an exemplary toilet paper roll holder vapor-dispensing device 100. Briefly, toilet paper roll holder vapor-dispensing device 100 is configured such that, when supporting a roll of toilet paper, device 100 generally mimics a standard toilet paper roll holder so as to make the device less noticeable and to allow normal access to the toilet paper. In this regard, while the illustrated embodiment is characterized by a generally circular cylindrical shape, it is to be understood that the present invention is not so limited. In various exemplary embodiments, the cylinder may be oval or otherwise shaped for functional or decorative purposes.

In its various embodiments, toilet paper roll holder vapor-dispensing device 100 is configured to be mounted, for example, between opposed sockets of a typical wall mounted structure and adapted for use in supporting a roll of toilet paper. In general, toilet paper roll holder device 100 suitably comprises a first portion 110, a second portion 120, a biasing mechanism 130, a material delivery system 150 (including volatizable material 140), and vents 115.

First and second portions 110 and 120 comprise any structures that support a toilet paper roll and that are configured to remain substantially stationary when paper is removed from the toilet paper roll. These structures may be made of plastic or another suitable material. First and second portions 110 and 120 may mimic typical plunger-type non-fragrance emitting toilet paper roll holders. For example, portions 110 and 120 may be cylindrical, with portion 110 sized to slide axially within portion 120, and wherein the cylindrical portions define an axis along the length of the toilet paper roll holder. Furthermore, portions 110 and 120 may comprise other suitable structures that support a roll of toilet paper and allow the roll to rotate about a substantially non-rolling structure. In another example, toilet paper roll holder vapor-dispensing device 100 may comprise a single, unitary structure with only one portion supporting the roll and containing the volatizable material and fragrance delivery system 120.

Portions 110 and 120 each include an end section (e.g., 111 or 121) configured to be received in a socket on a bracket, wall mounted structure, or other device configured to support a toilet paper roll holder. In one example, end sections 111 and 121 are configured to generate friction and substantially keep holder 100 from rolling when toilet paper is removed from the toilet paper roll. Furthermore, because free or substantially free rotation is not necessarily required to achieve an increased rate of fragrance delivery, portions 110 and 120 may be designed simply, i.e., without special ribs or other such elements that are generally used to cause the holder to rotate with the toilet paper roll. Furthermore, portions 110 and 120 may have different lug end configurations such that vapor-dispensing device 100 can support a roll of toilet tissue in a variety of decorative toilet tissue dispenser units, for example, such as those imitating Victorian styles and as exemplified in FIG. 12.

First and second portions 110 and 120 are held in an axially extended position by a biasing mechanism such as spring 130. Thus spring 130 is configured to resist compression, in the axial direction, of the two portions. In one exemplary embodiment, spring 130 is configured to maintain toilet paper roll holder 100 substantially stationary as a toilet paper roll rotates about holder 100. Spring 130 may, for example, engage an end surface or annular ring 112 on first portion 110 and engage an end surface 122 on second portion 120. In contrast to the special stress relaxation springs, and the like, used in some prior art rotatable toilet paper roll holders, spring 130 may comprise any suitable spring and in fact, may preferably comprise a spring selected to avoid relaxation. For example, spring 130 may be similar to those used in typical non-fragrance dispensing toilet paper roll holder, such as, for example, a simple wound steel wire spring.

Briefly, toilet paper roll holder 100 is further configured with one or more openings or vents 115 in portion 110 and/or portion 120. Vents 115 are configured to allow air circulation and diffusion to carry the fragrance from within the toilet paper roll holder to the environment surrounding the toilet paper roll holder. In accordance with an exemplary embodiment of the present invention, the vents are 4.75 millimeters in diameter and comprise 24–48 holes, although any other suitable size and/or number may be used depending on a particular application. Vents 115 are also configured to have any suitable shape and to be located on various parts of holder 100. For example, the vents may be slots rather than holes, and may preferably be at least ¼ inch in width and 1 to 1 ½ inches in length, although other dimensions may also be used. Fragrance activation and adjustment aspects related to vents 115 are described in further detail below.

As discussed above, holder 100 comprises a material delivery system 150 that includes a volatizable material 140. For example, in the context of an air freshener, volatizable material 140 comprises any suitable high intensity fragrance emitting substance. The term "high intensity" may be characterized in various different ways including human perception, rates of dispensation, and/or the like. For example, high intensity may be defined through testing of fragrance perception in a group of people. The intensity may include such factors as the ability to overcome certain odors. Other systems for characterizing high intensity fragrance may include the amount of fragrance material dispersed over a period of time. In one exemplary embodiment, volatizable material 140 comprises a scented oil. In this example, volatizable material 140 may be configured to emit fragrance material at a rate of 5 to 50 milligrams per hour, and preferably at a rate of 10–30 milligrams per hour, and most preferably at a rate of 15 milligrams per hour. Other rates may similarly characterize high intensity fragrance as the intensity may also depend on the type of fragrance, pungency of the fragrance, the material delivery system performance, and/or other factors in addition to the rate of material delivery. Other high intensity fragrance emitting substances may also be used in the present invention.

As discussed above, prior toilet paper roll holder fragrance delivery rates have been unsatisfactory due to the use of poor fragrance emitting substances. In prior art toilet paper roll holders, pellets of fragrance material, such as paradichlorobenzene or perfumed composites of ethylene and copolymers were used to supply fragrance. Using these relatively low fragrance emitting substances, prior art toilet paper roll holders had difficulty achieving a desirable fragrance dispensing intensity. However, instead of attempting to get more fragrance out of the old substances, it has been discovered that configuring the holder to use a high intensity fragrance substance facilitates the creation of simple and effective toilet paper roll holder vapor dispensers.

Volatizable material 140 is further configured such that a minor input, such as a disturbance, vibration, or light air flow, causes an increase in the output rate of fragrance vapors. Thus, vibrations may increase the output of fragrance material. These vibrations may occur due to the friction and bumping of the toilet paper roll as it rotates about the holder 100. In addition, the holder is configured such that the pulling of toilet paper from the roll and the rotation of the roll may cause a sufficient air flow change in the vicinity and within the toilet paper roll holder to momentarily increase the rate of fragrance delivery. The increase, in one exemplary embodiment, is 110% of the fragrance delivery rate during periods of non-removal of toilet paper.

Figure 2:
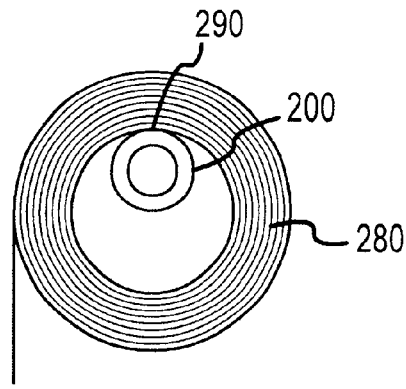
FIGS. 2 and 3 are end views of exemplary toilet paper rolls and roll holders in accordance with an exemplary embodiment of the present invention.
Figure 3:
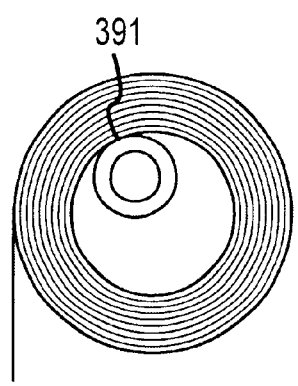

For example, FIG. 2 shows a toilet paper roll 280 at rest on a toilet paper roll holder 200 with a point of contact 290. When paper is pulled from the roll, as illustrated in FIG. 3, the point of contact moves to a second location 391. Thus, the removal of toilet paper may generate a somewhat random movement of the roll about the holder. This relative movement causes air to flow about and through the holder, thus momentarily increasing the rate of delivery of fragrance material. In particular, the relative movement by the roll of toilet paper causes air to momentarily displace on both sides of the holder. This action generally sets up momentary air flow around and/or through the holder. Accordingly, use of high intensity fragrance delivery substances makes it possible for small inputs, such as those discussed herein, to cause an appreciable increase in the fragrance delivery rate, where use of prior art toilet paper roll holder fragrance substances may not.

In accordance with another aspect of the present invention, the changing of a roll of toilet paper will generally result in the toilet paper roll holder being placed in a different rotational position. When this happens, the different rotational position may increase the level of fragrance output from the holder or otherwise improve its performance. For example, in the case of a high intensity scented oil transported by a porous wick, an increase may occur due to partitioning of fragrances with the heavier fragrance notes accumulating, over time, at the bottom side of the wick until the holder is repositioned. The repositioning may thus alleviate at least some of the accumulation and improve performance.

Figure 4:
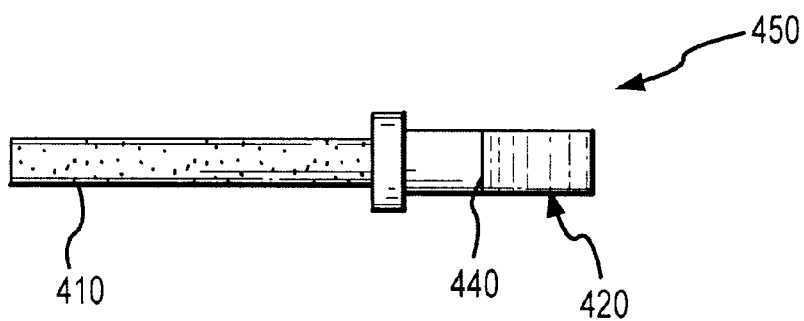
FIG. 4 is an exemplary material delivery system in accordance with an exemplary embodiment of the present invention.

Various exemplary material delivery systems are configured to convey volatizable material 140 to the surrounding environment and are particularly well-suited for high intensity scented oils. FIG. 4 illustrates one exemplary wick-reservoir material delivery system 450, comprising a wick 410, and a reservoir or ampoule 420. Reservoir 420 is configured to hold a volatile material such as fragrance oil 440. Briefly, reservoir 420 comprises any structure capable of holding a scented liquid (such as a scented oil) and small enough to fit within the toilet paper roll holder. For example, reservoir 420 may be a glass or plastic vial.

Wick 410 is configured to receive volatizable material 440 and to facilitate the dispersion of the material to the surrounding environment. For example, wick 410 is configured to draw volatizable material into a region that is exposed to the surrounding environment.

Therefore, wick 410 receives volatizable material through such mechanisms as the wicking of volatizable material 440 from reservoir 420. Wick 410 is made, for example, of a porous material such as graphite, porous plastic or other fibrous materials. Wick 410, in one exemplary embodiment is a porous plastic wick (type #1231 Porex with a diameter of 7 mm). Wick 410 is, for example, press-fit inside reservoir 420 with four centimeters of wick material exposed to the environment. Various wick dimensions may also be used. For example, the configuration of wick 410 may be suitably selected to increase or decrease surface area as desired.

In one embodiment, a large diameter, such as a one inch diameter, is used with a shorter wick while still achieving the same evaporation rate as a thin long wick. In various embodiments, wick 410 is positioned such that its length is substantially parallel to the axis of the toilet paper roll holder. In other embodiments, such as those illustrated in Figures 11 and 12, wick 410 may have a hollow core 411 which increases the surface area of wick 410.

The wick may comprise an insertion end and an exposed end wherein the insertion end of the wick has a first length and the exposed end of the wick has a second length. Although various lengths and proportions may be used, in an exemplary embodiment, ratio of the inserted length to exposed length may be anywhere from about 1:1 to about 1:5, or other useful ratios. In one exemplary embodiment, the wick is one inch in diameter, has an overall length of 1 ⅝ inches, and has an insertion depth of about ⅜ inch. The exposed end of the wick may include a central bore communicating with the environment. A cross-section through the wick may include a plurality of substantially semi-circular lobes.

Figure 5:
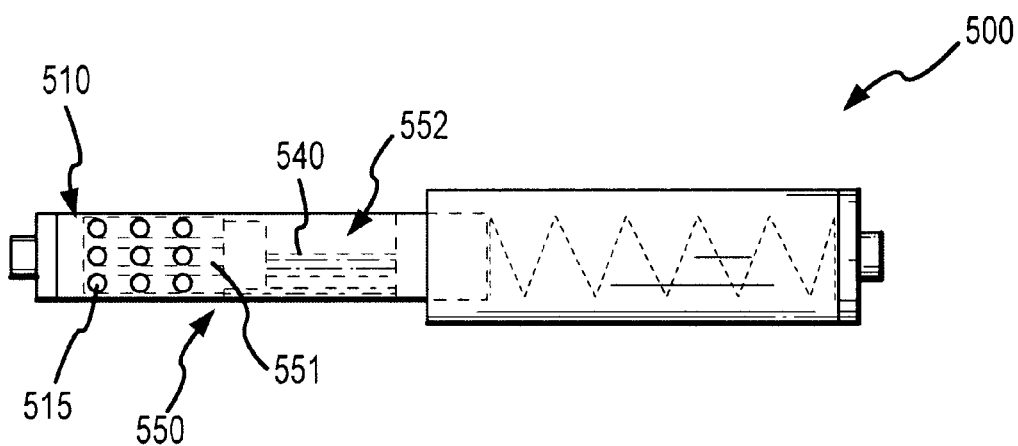
FIGS. 5–7 are exemplary toilet paper roll holders having exemplary material delivery systems in accordance with various embodiments of the present invention.

In one exemplary embodiment, a material delivery system of the type described with reference to FIG. 4 is illustrated in FIG. 5 installed in a toilet paper roll holder. In this embodiment, material delivery system 550 comprises a reservoir 552 containing a fragrance oil 540 as well as one or more wicks 551. Material delivery system 550 is inserted within holder 500 such that the entire device is press fit within the smaller of the two body portions (e.g., 510) and such that the wick is aligned with vents 515. Wick 551 is oriented substantially parallel to the axis of toilet paper roll holder 500.

Figure 6:
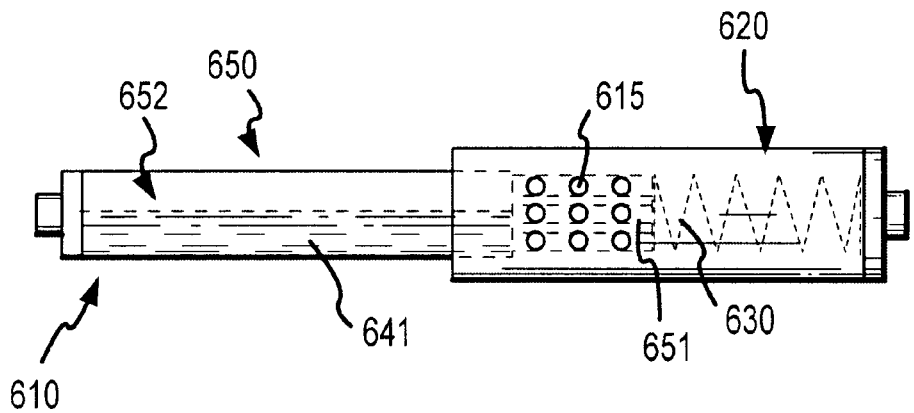

FIG. 6 illustrates another wick type material delivery system 650. In this exemplary embodiment, small portion 610 serves as the reservoir 652, which is configured to contain a fragrance oil 641. One or more wicks 651 are press fit into small portion 610 and oriented in proximity to vents 615 in large portion 620. As wick 651 shares the interior of large portion 620 with spring 630, spring 630 may be configured to encircle wick 615.

Figure 7:
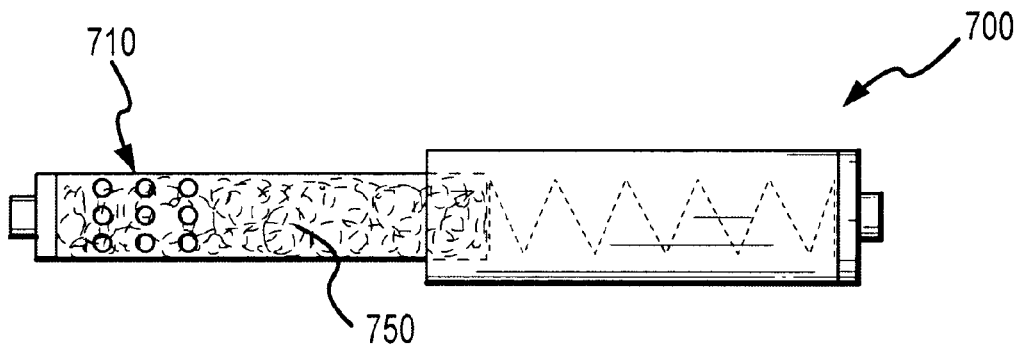

In other exemplary embodiments, other types of material delivery systems may be used. For example, with reference to FIG. 7, the material delivery system comprises a cellulose wading 750 that has been impregnated with a high intensity volatile material, such as, for example, a high intensity scented oil. Cellulose wading 750 may be located anywhere inside holder 700, but in this embodiment, the wading is shown loosely packed in the small portion 710. In like manner, cellulose wading 750 may be replaced with a blotter board, a high intensity fragrance impregnated plastic, a block of fragranced gel, either in a thermoform tray that contains the gel or cast into the end of the holder, or other similar material delivery systems. In another embodiment, a 60% to 80% fragrance/organic polymer resin matrix may be used as the gel in the thermo form tray. In other examples, material delivery system 150 further comprises a liquid reservoir sealed with a semi-porous membrane that allows metered evaporation of the fragrance.

In various embodiments of the present invention, vapor-dispensing device 100 is a "passive" vaporizer. Stated otherwise, the volatizable material of material delivery system 150 may volatize merely by exposure to ambient conditions (e.g., room temperature). Furthermore, evaporation may be further enhanced given that the temperature in a bathroom can be higher than the "room temperature" in the rest of the building. In some material delivery systems, the volatizable material might be in a "gel" and/or semi-permeable solid form that dispenses through mechanisms such as sublimation. Thus, it should be appreciated that any fragrance delivery mechanism now known or as yet unknown in the art can suitably be configured to be used in the present invention.

In particular, in each embodiment, the material delivery system and the volatizable material are configured to remain substantially stationary with respect to the toilet paper roll holder when paper is being removed from the roll. This stands in sharp contrast to many systems wherein tumbling of the fragrance bearing substance is necessary to generate fragrance output. Both material deliver system 150 and volatile substance 140 are configured to fit within the interior of toilet paper roll holder 100.

Holder 100 may be configured to retain fragrance during storage and/or shipping using various techniques. In one example, the entire assembly is shrink-wrapped. In another embodiment, the holder is configured to seal-off vents 115 when in a closed position. FIG. 8 illustrates an exemplary holder 800 in a closed position 870 and an open position 880. In closed position 870, vents 815A are covered by second portion 820 and vents 815B are covered by the first portion 810. In open position 880, both sets of vents are open. In this example, holder 800 is maintained in closed position 870 by any suitable technique. For example, a latch, hook, or other device may retain the holder in closed position 870. The device may be unlocked and released by a quarter turn of one of the two portions of toilet paper holder 800. While various lock/unlock methods may be used, in one embodiment, various pop-up pump locking techniques is used. For example, a latch, hook, threads, or a lug/cam arrangement, or other closure configuration may be used to retain the assembly in a closed and/or sealed position until activated.

FIG. 9 illustrates another exemplary holder, wherein holder 900 is configured with a cap structure configured to retain fragrance during storage and/or shipping. Cap structure 990 is configured to cover vents 915 in closed position 970. Cap structure 990 is removed in open position 980. For example, cap structure 990 may screw or slide onto and off of large portion 920. Other activation techniques may also be employed, whereby fragrance is retained during shipment and/or storage. For example, with reference to FIG. 10, an internal bayonet 1001 is used to puncture a membrane and start the flow of fragrance oil 1041 to a wick 1051.

In accordance with an exemplary embodiment of the present invention, vents 115 are suitably configured to be adjustable to varying apertures. Such holders, having variable aperture control, are configured to increase or decrease the amount of fragrance dispensed depending on user desired performance, room size and the like. In accordance with various aspects of the present invention, an arrangement of holes are suitably configured in both portions 110 and 120 to vary the percentage of openings from the environment to the inside of the toilet paper roll holder by relative positioning of the two portions. In one embodiment, variation in the size and/or number of openings may occur by twisting the two portions of the toilet paper roll holder relative to each other. In this example, holes are configured in the first and second portions 110 and 120 such that turning the two portions relative to each other about the axis of the holder can result in overlapping of the vents. Thus, fragrance output can be turned off, or adjusted to a desired intensity.

In accordance with an exemplary embodiment of the present invention, holder 100 is configured to seal in fragrance prior to activation. For example, holder 100 is configured to have a seal between portions 110 and 120. In this embodiment, the seal is configured to prevent fragrance vapors from escaping the interior of the toilet paper roll holder, prior to activation, through the gap between the mating surfaces of portions 110 and 120. In one exemplary embodiment, the seal is formed using an O-ring 160 configured about small portion 110 and compressed between one end of large portion 120 and an annular ridge on portion 110. Other suitable devices may also be used for creating a seal. Thus, in an exemplary embodiment, fragrance vapors are only introduced to the environment through vents 115.

The passive vapor-dispensing apparatus, in various exemplary embodiments, further comprises an end-of-life indicator. The end-of-life indicator is configured to allow an individual to observe when the holder has substantially exhausted the fragrance material. In contrast to pellets or gels which generally look the same before and after the fragrance material is spent, an end-of-life indicator allows a user to clearly see how much life remains on the air freshening device. For example, in one wick and oil embodiment, an end-of-life indicator comprises a view structure in one of the first or second housing portions enabling view of the remaining amount of oil. In an exemplary embodiment, clear plastic parts permit easy viewing of the amount of oil remaining in the fragrance vial. The molded plastic parts may be frosted in some areas to promote viewing of the fragrance vial and to obscure other portions of the interior. Frosting may be accomplished by selective sandblasting and roughening up of portions of the steel molds used to create the toilet paper holder plastic parts. Other materials may also be used with other viewing structures.

Figure 11:
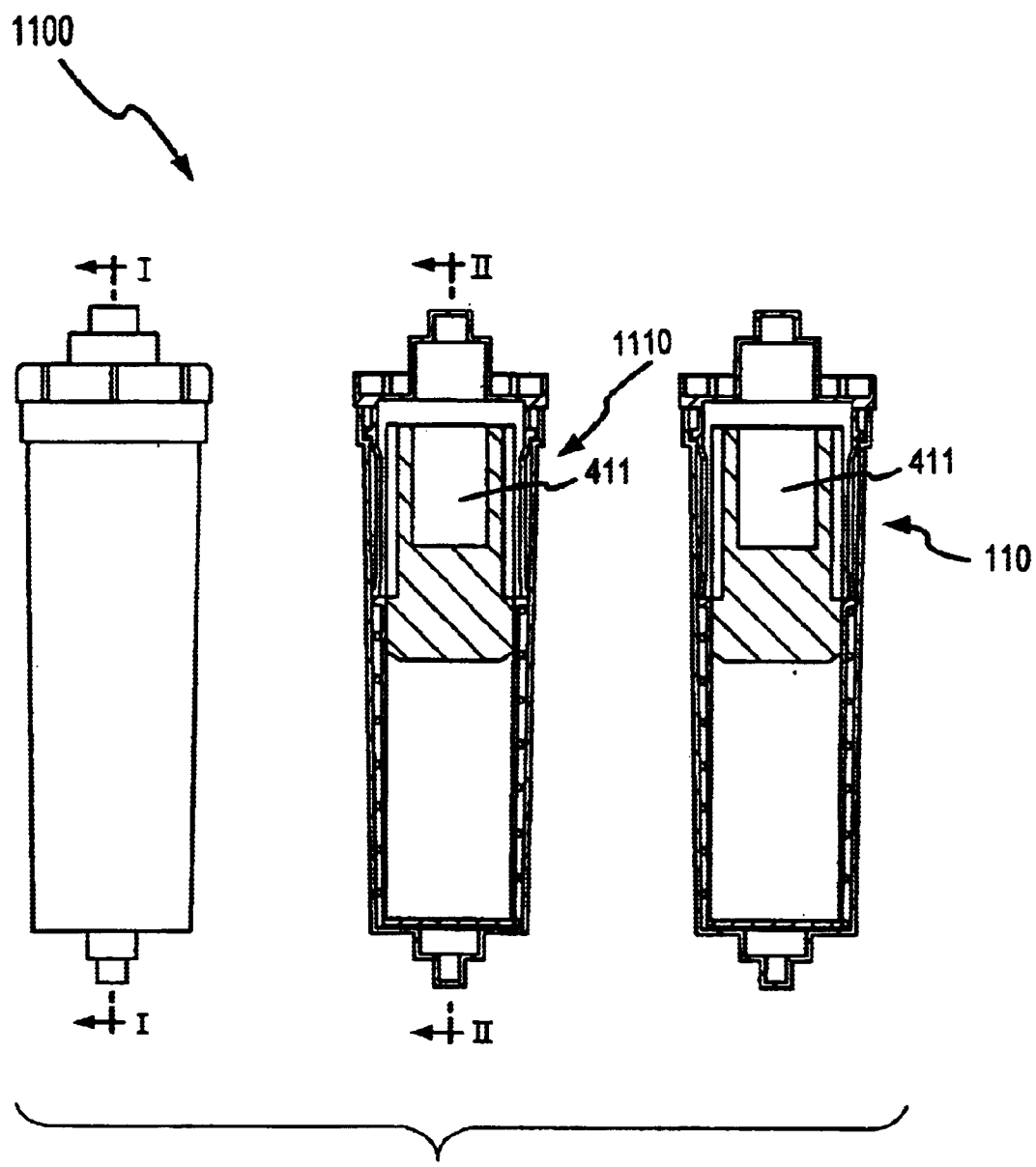
FIGS. 11–12 are another exemplary toilet paper roll holder having an exemplary material delivery system in accordance with another exemplary embodiment of the present invention.
Figure 12:
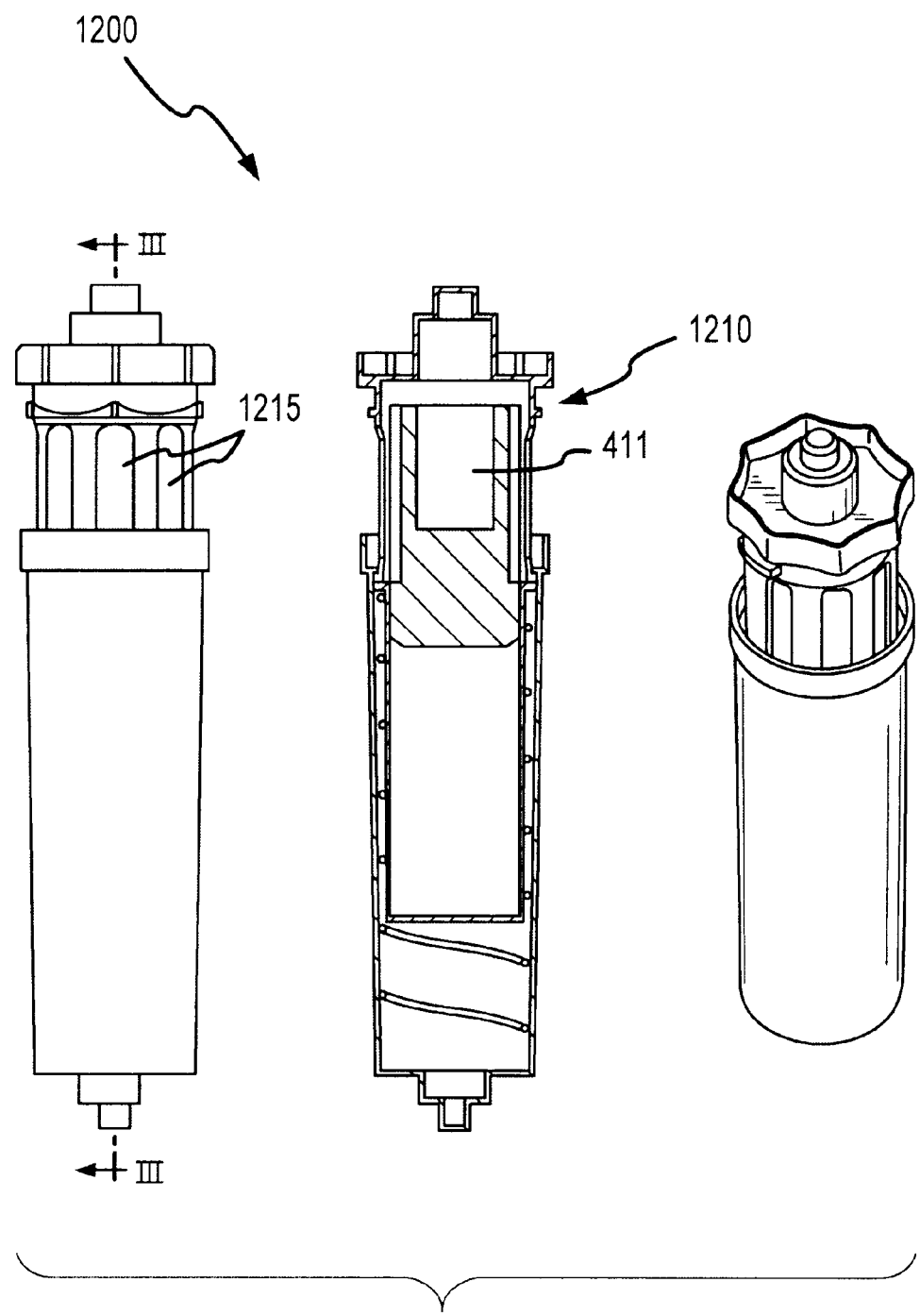

FIGS. 11 and 12 illustrate a further exemplary embodiment of the present invention in both the closed position (FIG. 11) and open position (FIG. 12). In an exemplary embodiment, vents 1215 are illustrated as slots. Toilet paper roll holders 1100 and 1200 may also comprise one or more seals 1110 and 1210, configured to contain the volatizable material within the holder until it is activated.

Finally, the present invention has been described above with reference to various exemplary embodiments. However, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices. These and other changes or modifications are intended to be included within the scope of the present invention.

A toilet paper roll holder vapor-dispensing device is configured with an internal material delivery system and high intensity volatizable material. A toilet paper roll holder vapor-dispensing device is configured with adjustable vents and may also be configured to increase dispensation of a fragrance when toilet paper is taken off the toilet paper roll through a number of configurations such as using high intensity fragrance (e.g., scented oil). The toilet paper roll holder is configured to be substantially stationary when toilet paper is removed from a roll of toilet paper supported by the holder.

We claim:

1. A vapor-dispensing toilet paper roll holder apparatus for holding a toilet paper roll, the apparatus comprising:

a first housing portion;

a second housing portion;

a spring configured to hold said first and second housing portions in axial extension and to substantially prevent rotation of said toilet paper roll holder when toilet paper is being removed from the toilet paper roll;

at least one vent in at least one of said first and second housing portions;

a material delivery system contained within said toilet paper roll holder having a volatizable material, wherein said volatizable material remains substantially stationary with respect to said first and second housing portions when removing toilet paper from the toilet paper roll, and wherein removing toilet paper from the toilet paper roll on said toilet paper roll holder increases volatization of said volatizable material;

wherein said first and second housing portions are configured to be adjustable relative to each other to create at least an open position and a closed position, wherein in said closed position all of the at least one vents in said housing are covered to create a temporary barrier between said volatizable material and an external environment, and wherein in said open position at least one of said at least one vent is substantially open to allow said volatizable material to escape to the external environment; and wherein the apparatus is activated by adjusting said first housing portion relative to said second housing portion to said open position from said closed position.

2. The vapor-dispensing apparatus of claim 1, wherein said volatizable material comprises a high intensity fragrance component.

3. The vapor-dispensing apparatus of claim 2, wherein said material delivery system comprises a wick oriented substantially co-axial with the axis of said toilet paper roll holder.

4. The vapor-dispensing apparatus of claim 3, wherein said wick is a porous plastic wick.

5. The vapor-dispensing apparatus of claim 4, wherein said porous plastic wick has an average pore size of between approximately 25 and 30 microns.

6. The vapor-dispensing apparatus of claim 3, wherein said material delivery system is configured to passively deliver said fragrance component into an environment in the form of a high-intensity vapor at a rate of between approximately 10.0 mg/hr and approximately 30.0 mg/hr.

7. The apparatus of claim 3, wherein said material delivery system is configured to passively deliver said fragrance component into said environment at a rate of approximately 15 mg/hr.

8. The apparatus of claim 3, wherein said material delivery system is configured to, during removal of paper from the roll, passively deliver said fragrance component into the environment at a rate that is 110% of the rate of dispensation when the roll is at rest.

9. The vapor-dispensing apparatus of claim 3, said volatizable material having a flash point of between approximately 100° F. and 180° F., a vapor pressure within said housing of between approximately 0.01 and 0.5 mmHg, and a mass ratio of said fragrance component to said volatizable material of at least approximately 75%.

10. The passive vapor-dispensing apparatus of claim 2, wherein said material delivery system comprises a blotter-board and wherein said blotter-board is saturated with said volatizable material and placed within at least one of said first and said second housings.

11. The passive vapor-dispensing apparatus of claim 2, wherein said material delivery system comprises a cellulose wading and wherein said cellulose wading is saturated with said volatizable material and placed within at least one of said first and said second housings.

12. A vapor-dispensing toilet paper roll holder apparatus for holding a toilet paper roll, the apparatus comprising:
   a first housing portion;
   a second housing portion;
   a spring configured to hold said first and second housing portions in axial extension and to substantially prevent rotation of said toilet paper roll holder when toilet paper is being removed from the toilet paper roll;
   at least one vent in at least one of said first and second housing portions;
   a material delivery system contained within said toilet paper roll holder having a volatizable material, wherein said volatizable material remains substantially stationary with respect to said first and second housing portions when removing toilet paper from the toilet paper roll, and wherein removing toilet paper from the toilet paper roll on said toilet paper roll holder increases volatization of said volatizable material;
   wherein said at least one vent further comprises an adjustable venting structure comprising:
      a first set of vents in said first housing portion;
      a second set of vents in said second housing portion, wherein said second housing portion is axially rotatable with respect to said first housing portion; and
      said adjustable venting structure having a maximum setting when said first set of vents and said second set of vents are aligned to produce a maximum opening, and a minimum setting when said first set of vents and said second set of vents are substantially misaligned.

13. The vapor-dispensing apparatus of claim 12, wherein said minimum setting corresponds to a an opening of approximately 0%, and said maximum setting corresponds to an opening of approximately 30% of the total external surface area of said combined housings.

14. The passive vapor-dispensing apparatus of claim 12, wherein said material delivery system comprises a tray and wherein said tray supports a gel volatizable material.

15. A passive vapor-dispensing toilet paper roll holder apparatus comprising:
   a first housing portion;
   a second housing portion, wherein said first and second housing portions are configured to align axially with axial adjustment relative to each other, wherein at least one of said first and second housing portions comprises at least one vent;
   a material delivery system comprising a volatizable material and a wick, wherein said material delivery system is contained within said toilet paper roll holder; wherein a first end of said wick is immersed in said volatizable material, and wherein said wick is oriented substantially parallel to the axis of said toilet paper roll holder;
   a spring configured to hold said first and second housing portions in an extended axial position and configured to substantially prevent rotation of said toilet paper roll holder;
   wherein said first and second housing portions are configured to be adjustable relative to each other to create at least an open position and a closed position, wherein in said closed position all of the at least one vents in said housing are covered to create a temporary barrier between said volatizable material and an external environment, and wherein in said open position at least one of said at least one vent is substantially open to allow said volatizable material to escape to the external environment; and
   wherein the apparatus is activated by adjusting said first housing portion relative to said second housing portion to said open position from said closed position.

16. The passive vapor-dispensing apparatus of claim 15, wherein said material delivery system is configured to deliver an increased amount of fragrance when toilet paper is removed from the toilet paper roll.

17. The passive vapor-dispensing apparatus of claim 15, wherein said wick comprises a porous plastic material.

18. The passive vapor-dispensing apparatus of claim 17, wherein said material delivery system further comprises a reservoir and wherein said wick is press fit into said reservoir.

19. The passive vapor-dispensing apparatus of claim 17, wherein at least one of said first and said second housing portions comprises an end-of-life indicator comprising a viewing structure enabling view of the remaining amount of said volatizable material.

20. A vapor-dispensing toilet paper roll holder apparatus comprising:
   a first housing portion;
   a second housing portion:
   at least one vent in at least one of said first and second housing portions;
   a reservoir containing a high intensity fragrance oil and located within said toilet paper roll holder;
   a wick located within said toilet paper roll holder and configured to deliver said high intensity fragrance oil in the form of a vapor, said wick having a first portion and a second portion, said first portion extending into said reservoir, wherein said wick is oriented substantially parallel to the axis of said toilet paper roll holder; and
   a spring configured to maintain said first and second portions in an axially elongated position, and configured to substantially prevent the rotation of said toilet paper roll holder; and
   wherein said first and second housing portions are configured to be adjustable relative to each other to create at least an open position and a closed position, wherein in said closed position all of the at least one vents in said housing are covered to create a temporary barrier between said volatizable material and an external environment, and wherein in said open position at least one of said at least one vent is substantially open to allow said volatizable material to escape to the external environment.

21. The apparatus of claims 20 wherein the apparatus is activated by adjusting said first housing portion relative to said second housing portion to said open position from said closed position.

22. The apparatus of claim 21, wherein said adjustment involves a pop-open mechanism.

23. The apparatus of claim 21, further comprising a screw cap configured to mate with said second housing for enclosing said first housing, wherein said first housing comprises said at least one vent.

24. The apparatus of claim 20 wherein both said first and said second housing portions comprise at least one vent, wherein said first housing portion is axially rotatable with respect to said second housing portion, wherein said first and second housing portions are configured such that an axial rotation adjustment of said first housing portions relative to said second housing portion facilitates a variable range of exposed vents.

25. The apparatus of claim 24 wherein the apparatus is activated by adjusting said first housing portion relative to said second housing portion from a position where all vents are closed to a position where at least some of said vents are open.

26. The apparatus of claim 20 further comprising a bayonet configured to activate the dispensing of said volatizable material.

27. The apparatus of claim 20, further comprising a seal configured to prevent said volatizable material from passing out of said holder when in a closed position.

28. The apparatus of claim 27, wherein said seal is an o-ring.

29. A vapor-dispensing toilet paper roll holder apparatus for holding a toilet paper roll, the apparatus comprising:

a first housing portion;

a second housing portion;

a spring configured to hold said first and second housing portions in axial extension and to substantially prevent rotation of said toilet paper roll holder when toilet paper is being removed from the toilet paper roll;

at least one vent in at least one of said first and second housing portions; and a material delivery system contained within said toilet paper roll holder having a volatizable material, and wherein said volatizable material remains substantially stationary with respect to said first and second housing portions when removing toilet paper from the toilet paper roll;

wherein said first and second housing portions are configured to be adjustable relative to each other to create at least an open position and a closed position, wherein in said closed position all of the at least one vents in said housing are covered to create a temporary barrier between said volatizable material and an external environment, and wherein in said open position at least one of said at least one vent is substantially open to allow said volatizable material to escape to the external environment; and wherein the apparatus is activated by adjusting said first housing portion relative to said second housing portion to said open position from said closed position.

30. The vapor-dispensing apparatus of claim 29, wherein said material delivery system comprises a wick oriented substantially co-axial with the axis of said toilet paper roll holder.

* * * * *